United States Patent [19]

Hughes et al.

[11] Patent Number: 5,783,397
[45] Date of Patent: Jul. 21, 1998

[54] SCREENING NATURAL SAMPLES FOR NEW THERAPEUTIC COMPOUNDS USING CAPILLARY ELECTROPHORESIS

[75] Inventors: Dallas E. Hughes, Dover; Barry L. Karger, Newton, both of Mass.

[73] Assignee: Northeastern University, Boston, Mass.

[21] Appl. No.: 662,085

[22] Filed: Jun. 12, 1996

Related U.S. Application Data

[60] Provisional application No. 60/008,503, Dec. 11, 1995.
[51] Int. Cl.$^6$ ............................ G01N 33/53; G01N 33/00; G01N 21/00; C25D 13/00
[52] U.S. Cl. .................. 435/7.1; 435/4; 435/5; 435/6; 435/7.8; 435/7.9; 435/7.2; 204/299; 204/180.1; 204/407; 356/344; 436/6
[58] Field of Search ............ 435/7.1, 5, 4, 7.8, 435/7.9, 7.2, 6; 204/299, 180.1, 182.8, 407; 356/344; 436/536

[56] References Cited

U.S. PATENT DOCUMENTS

| | | | |
|---|---|---|---|
| 5,234,586 | 8/1993 | Afeyan et al. | 210/198.2 |
| 5,324,401 | 6/1994 | Yeung et al. | 204/180.1 |
| 5,431,793 | 7/1995 | Wang et al. | 204/182.8 |
| 5,532,124 | 7/1996 | Block et al. | 435/5 |
| 5,534,410 | 7/1996 | Tjian et al. | 435/6 |
| 5,536,382 | 7/1996 | Sunzeri | 204/451 |
| 5,567,282 | 10/1996 | Wang et al. | 204/450 |

FOREIGN PATENT DOCUMENTS

| | | |
|---|---|---|
| 9106850 | 5/1991 | European Pat. Off. . |
| 581413 | 2/1994 | European Pat. Off. . |
| 9417409 | 4/1994 | European Pat. Off. . |
| 9520160 | 7/1995 | European Pat. Off. . |

OTHER PUBLICATIONS

Yen-Ho Chu et al., "Affinity Capillary Electrophoresis-Mass Spectrometry for Screening Combinatorial Libraries", *J. Am. Chem. Soc.* vol. 118:7827-7835 (1996).

Chu et al., "Using Affinity Capillary Electrophoresis To Identify the Peptide in a Peptide Library that Binds Most Tightly to Vancomycin," *J. Org. Chem.* 58:648-652 (1993).

Chu et al., "Using Affinity Capillary Electrophoresis To Determine Binding Stoichiometries of Protein-Ligand Interactions," *Biochemistry* 33:10616-10621 (1994).

Chu et al., "Affinity Capillary Electrophoresis," *Acc. Chem. Res.* 28:461-468 (1995).

Crothers, "Gel electrophoresis of protein-DNA complexes," *Nature* 325:464-465 (1987).

Ceglarek et al., "Studies of DNA-protein interactions by gel electrophoresis," *Electrophoresis* 10:360-365 (1989).

Fried et al., "Measurement of protein-DNA interaction parameters by electrophoresis mobility shift assay," *Electrophoresis* 10:366-376 (1989).

Xian et al., "DNA-protein binding assays from a single sea urchin egg: A high-sensitivity capillary electrophoresis method," *Proc. Natl. Acad. Sci. USA* 93:86-90 (1996).

Heegaard et al., "Use of Capillary Zone Electrophoresis To Evaluate the Binding of Anionic Carbohydrates to Synthetic Peptides Derived from Human Serum Amyloid P Component," *Anal. Chem.* 64:2479-2482 (1992).

Wagner et al., "Use of Affinity Capillary Electrophoresis To Measure Binding Constants of Ligands to Proteins," *J. Med. Chem.* 35:2915-2917 (1992).

Shimura et al., "Affinity Probe Capillary Electrophoresis: Analysis of Recombinant Human Growth Hormone with a Fluorescent Labeled Antibody Fragment," *Anal. Chem.* 66:9-15 (1994).

Sun et al., "Enhanced albumin protein separations and protein-drug binding constant measurements using anti-inflammatory drugs as run buffer additives in affinity capillary electrophoresis," *Journal of Chromatography* 661:335-340 (1994).

Heegard, "Determination of antigen-antibody affinity by immuno-capillary electrophoresis," *Journal of Chromatography* 680:405-412 (1994).

Liu et al., "Affinity capillary electrophoresis applied to the studies of interactions of a member of heat shock protein family with an immunosuppressant," *Journal of Chromatography* 680:395-403 (1994).

Pritchett et al., "Capillary Electrophoresis-Based Immunoassays," *Bio/Technology* 13:1449-1450 (1995).

Koutny et al., "Microchip Electrophoretic Immunoassay for Serum Cortisol," *Anal. Chem.* 68:18-22 (1996).

(List continued on next page.)

*Primary Examiner*—Lila Feisee
*Assistant Examiner*—Susan Ungar
*Attorney, Agent, or Firm*—Weingarten, Schurgin, Gagnebin & Hayes LLP

[57] ABSTRACT

A method in which natural sample components are simultaneously fractionated and screened for compounds that bind tightly to specific molecules of interest is disclosed. Such newly isolated ligands are good candidates for potential therapeutic or diagnostic compounds. The natural sample is first combined with a potential target molecule and then subjected to capillary electrophoresis (CE). Charged (or even neutral) compounds present in the natural sample that bind to the added target molecule can alter its normal migration time upon CE, by changing its charge-to-mass ratio, or will cause a variation in peak shape or area. Complex formation can be detected by simply monitoring the migration of the target molecule during electrophoresis. Any new ligands that bind to the target molecule will be good candidates for therapeutic or diagnostic compounds. Interfering, weak-binding ligands commonly present in crude extracts are not detected. Small, neutral ligands, as well as charged ligands, can be identified in competitive binding experiments with known, charged competitor molecules.

26 Claims, 12 Drawing Sheets

OTHER PUBLICATIONS

Chu et al., "Free Solution Identification of Candidate Peptides from Combinatorial Libraries by Affinity Capillary Electrophoresis/Mass Spectrometry," *J. Am. Chem. Soc.* 117:5419–5420 (1995).

Z. Deyl et al, J. Chromatogr (1994) 656(1) 3–27.

Chu et al., J. Med. Chem. (1992) 35:2915–2917.

Dent & Latchman, DNA mobility Shift Assay in Transcription Factors, Oxford Univ Press, Oxford pp. 1–26.

Ueno & Yeung, Analytical Chem. (1994) 66: 1424–1431.

Perkins & Tomer, Analytical Chemistry, 1994, 66: 2835–2840.

Avila et al, J. Med. Chem. 1993, 36: 126–133.

Lakin, Transcription Factors, Oxford Univ. Press, Oxford, pp. 27–29.

Gordon et al, Analytical Chem., 1994 66: 2835–2840.

Mayer et al, Anal Chem, 1994, 66:1777–1780.

Schmalzing, Anal Chem. 67: 606–612, 1995.

5,783,397

SCREENING NATURAL SAMPLES FOR NEW THERAPEUTIC COMPOUNDS USING CAPILLARY ELECTROPHORESIS

This application claims the benefit of U.S. Provisional Application Ser. No. 60/000,503 filed on Dec. 11, 1995.

FIELD OF THE INVENTION

This invention relates to screening complex natural samples for new drug compounds and in particular, to using capillary electrophoresis for such screening.

BACKGROUND OF THE INVENTION

Developing screens to identify new drug compounds in natural samples presents some unique and difficult challenges. Major problems include low concentrations of active compounds, unknown components that can interfere with screens, and compound identification once a positive sample is obtained. Despite these obstacles, the pharmaceutical industry still maintains a strong interest in natural product screening. It is widely recognized that nature provides a virtually endless supply of new chemical structures that are often difficult or impossible to synthesize in a cost-effective manner. Most natural products have some bioactivity, and historically, natural products and their analogs have been the most successful source of pharmaceutical compounds.

Screening technologies for therapeutic natural products fall into two broad categories, bioassays and mechanism-based assays (Gordon et al., J. Med. Chem. 37:1386–1401, 1994). Bioassays are the oldest, and so far most productive, screening tool. Bioassays measure the effect of natural samples on the viability or metabolism of disease-related cell types such as bacteria, fungi, viruses, and tumor cells. For example, the β-lactam antibiotics (e.g., penicillins and cephalosporins) were discovered by testing microbial broths for bacterial growth inhibition in culture tests. Likewise, the antifungal compounds nystatin and amphotericin B were isolated from broths that inhibited growth of yeast in culture tests. However, mainly due to their lack of specificity and sensitivity, most bioassays have been replaced as primary screens with more sophisticated, mechanism-based assays.

Mechanism-based assays can be subdivided into three general categories: recombinant cell-based assays, enzymatic (biochemical) assays, and binding assays. Today's assays are designed with the need for high throughput capacity so they must be robust, simple, and amenable to automation in a parallel processing mode.

Recombinant, cell-based assays screen for some known functional response. Usually a target receptor, enzyme, or other protein is introduced into cultured cells by genetic engineering. Inhibition or induction of target activity is associated with an easily-measured response. For example, modifiers of transcription factors (TF) can be measured by fusing the TF's target DNA sequence (enhancer or promoter) to a luciferase (light-producing) gene. TF agonists result in transcription of the luciferase gene, and light is produced. If an antagonist is present, light is not produced. One advantage of cell-based assays over enzymatic and binding assays is that they may provide more physiologically appropriate leads because intact cells are used. On the other hand, these screens can be very difficult to develop, can be slow and are quite variable (Janzen et al., Society for Biomolecular Screening Meeting, Nov. 7–10, 1995).

Enzymatic assays are cell-free screens that directly or indirectly test the effect of soluble compounds on the activity of purified target molecules. For example, viral reverse transcriptase inhibitors can be screened by measuring the incorporation of radiolabeled thymidine into a growing DNA chain from a polyuridine RNA template. These assays can be very sensitive and are amenable to automation using microtiter plates. For natural product screening, however, unknown compounds in the samples can dramatically interfere with the results, leading to unacceptably high levels of false negatives and false positives. For example, greater than 15% of aqueous extracts from terrestrial plants, cyanobacteria, marine invertebrates, and algae exhibit positive activity in HIV antiviral screens due to interfering compounds such as plant tannins (Cardellina et al., J. Nat. Prod. 56:1123–1129, 1993).

Binding assays are particularly useful for screening soluble mixtures for compounds that bind, and thus potentially inhibit, target therapeutic molecules. The target molecule (usually a protein) can be affixed or tethered to a solid substrate such as the sides of microtiter wells, beads, or chromatographic supports. If the target molecule is a receptor, it can be expressed in the membrane of a cell, which is attached to the solid support. The samples are incubated with the immobilized targets, and bound ligands are detected, usually through an associated colorometric or fluorescent reaction. Alternatively, the sample is mixed with a soluble-phase target that is captured using an anti-target antibody. Such binding assays are advantageous as they facilitate the washing and isolation of target-ligand complexes. However, they suffer from several disadvantages, particularly for natural product screening. One problem is that multiple, weak-binding, background compounds, if present in sufficient quantities, can give a positive signal. Therefore, improved clean-up capability is desirable unless heavy washing is possible. Another general problem with immobilized-target binding assays is that affixing target proteins to solid substrates often results in a functional change or inactivation of the protein. This problem could be addressed to some extent by inserting some inert "handle" such as a peptide epitope into the target by recombinant DNA technology. The protein-ligand complex could then be isolated through the use of an antibody to this epitope. However, developing these artificial targets is time-consuming and expensive. A disadvantage of the commonly used microtiter (ELISA) format is that the target molecule, which is usually attached to the well wall, is not in contact with most of the soluble sample dispersed throughout the well, which results in the need for increased reaction times. Some improvements have been made through using reduced reaction volumes.

Despite the difficulties, binding assays remain a major screening tool in the drug discovery efforts of pharmaceutical and biotechnology companies. This is because many successful drugs act by binding tightly to essential molecules of key metabolic pathways. Examples include the anticancer agents taxol and daunomycin, the antigout agent colchicine, and the antithrombolytic agent hirudin and its analogs.

Due to rapid progress in genomics, hundreds of disease-related genes and their corresponding proteins will be discovered in the near future (Bevan et al., Trends in Biotechnology 13:115–121, 1995). These elements will add to the current inventory of therapeutic targets for affinity binding assays. Developing rapid and cost-effective screening tools that can take advantage of these targets is a critical and evolving goal in the drug discovery business.

SUMMARY OF THE INVENTION

The method of the invention uses capillary electrophoresis (CE) to combine a partial purification step with a solution-based affinity assay to discover new active compounds, e.g., potential new drugs or diagnostic compounds, from complex biological material, particularly natural samples (NS). This method is able to overcome major problems associated with current pharmaceutical screens such as poor detection levels and low sensitivity caused by interfering compounds present in complex natural samples. Furthermore, the method of the invention is capable of uncovering drug activity in samples where such activity had previously been unobserved using other primary screening methods.

In the method of the invention, components of complex biological material, e.g., from natural samples, are simultaneously fractionated and screened for new compounds that bind tightly to specific molecules of interest. Such newly isolated ligands are good candidates for potential therapeutic or diagnostic compounds. This single-step assay requires very small amounts of sample and utilizes a highly specific, solution-based affinity assay, thus facilitating the identification of a true positive sample as well as avoiding interfering background components.

In one application of the invention, the sample of complex biological material, e.g., natural sample, is first combined with a known target molecule and then fractionated by CE, while the migration of the target molecule is tracked. Charged compounds present in the natural sample that bind tightly to the target molecule will alter its normal migration time or cause a change in peak shape or area by changing its charge-to-mass ratio or overall structure. Complex formation can be detected by simply tracking the target molecule during electrophoresis and comparing its migration pattern or electrophoretic profile in the presence of a natural sample to that in the absence of the sample. Any ligands that bind to the target molecule are candidates for therapeutic lead compounds or diagnostic compounds.

In another aspect of the method, small, neutral ligands as well as charged ligands can be identified in competitive binding experiments using known, charged competitor molecules. A competitor-target molecule complex or unbound competitor can be observed to have a specific migration time, as a reference standard. Any ligands in the natural sample that are bound tightly to the target molecule do not allow the competitor to interact with the target, thus changing the observed mobility of the target molecule.

Thus, in general, the method of the invention for screening complex biological material for new active compounds includes providing a sample of complex biological material, combining the sample with a target molecule, injecting a sample from the previous step into an apparatus for capillary electrophoresis, subjecting the sample to capillary electrophoresis and monitoring the migration of the labeled or unlabeled target molecule upon electrophoresis (either directly or indirectly). Preferably, the method also includes comparing the migration of the target to the migration of a reference standard. A reference standard is usually an analyte with a known migration time which is used as an internal control to determine whether the migration of the target or competitor ligand changed in the presence of complex biological sample. For example, the reference standard can be an excess of unbound target or competitor ligand-shifted target, an excess of competitor ligand, an independent non-interacting molecule, or even a range of time in which the target or competitor ligand normally runs in the absence of complex biological sample.

In a further application of the method of the invention, to subtractive analysis, all possible detectable compounds in a sample of complex biological material that is to be screened are detected by a specific method to serve as a reference standard, following capillary electrophoresis of the sample. An additional sample of the biological material to be screened is then combined with a potential target molecule, the combined material is fractionated by CE, and all compounds are again detected by the same detection method. Any compounds detected in the reference standard sample that are not among the compounds detected (by the same method) following electrophoresis of the combined material are candidate products for further analysis as new, useful ligands of the target molecule.

Once detected, the binding ligands may be isolated and tested for, e.g., their therapeutic efficacy and pharmacokinetic properties. With the use of dye-conjugated molecules and laser-induced fluorescence, the method of the invention provides the ability to detect ligand concentrations, directly in the sample, in the low nanomolar range, which is substantially lower than the micromolar concentrations that are the limit in most current natural product screens. In addition, washing of the capillary and replacement of the buffer or matrix in a capillary electrophoresis system is rapid and allows higher throughput of crude natural samples than is possible with standard procedures based on affinity chromatography.

The method of the invention will permit the rapid detection of potentially useful, new molecules in natural samples that escape standard screens due to low concentrations and/or the presence of interfering compounds. The small scale of CE has major advantages in that the quantity of rare or potentially hazardous assay components, e.g., the natural sample itself, the target molecule or the buffers used, can be reduced considerably.

The method of the invention will accommodate high-throughput screening of natural samples suitable for automation by employing multiple capillaries or multiple channels on microfabricated devices and several target molecules per channel or capillary. In many cases, on-line structural information of lead candidates can be directly ascertained by coupling a mass spectrometer, or other analytical device such as NMR, directly to the capillary or channel.

Other features and advantages of the invention will be apparent from the following description of the preferred embodiments thereof.

BRIEF DESCRIPTION OF THE DRAWINGS

FIG. 3 shows capillary electrophoresis of thrombin in the presence and absence of its natural inhibitor hirudin as an example of the model for the method of the invention shown in FIG. 2a;

FIG. 4 shows capillary electrophoresis of thrombin in the presence and absence of a thrombin-binding aptamer as an additional example of the model shown in FIG. 2a;

DETAILED DESCRIPTION OF THE INVENTION

Capillary electrophoresis (CE) has gained widespread utility as an efficient analytical/separation tool that combines high resolution, low detection levels, speed, and convenience. The method of the invention is a novel application of CE, discovering new compounds from natural samples using an affinity-based capillary electrophoresis method. The method of the invention overcomes major problems associated with current pharmaceutical screens of natural sources, such as poor detection levels, low selectivity, and low sensitivity caused by interfering compounds present in the complex samples. In the method of the invention, these problems are solved because natural samples are simultaneously separated from interfering compounds and screened for compounds that bind tightly to specific molecules of interest.

Figure 1:
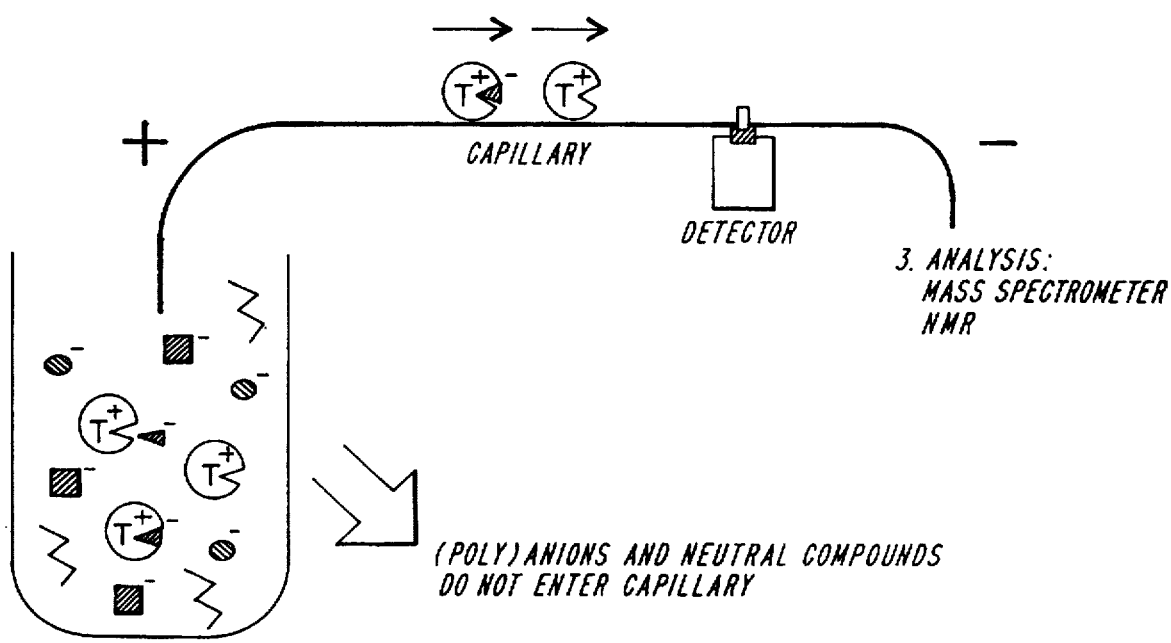
FIG. 1 shows one general model for isolating new ligands from natural samples according to the method of the invention.

In one aspect of the method, the natural sample is first combined with a known target molecule (see examples given below) and then fractionated by CE. As shown in FIG. 1, charged compounds present in the natural sample bind, in the first phase of the method, to the added target molecule. The method of the invention is designed to detect those compounds that bind most tightly. The bound, charged compounds alter the normal migration time of the target molecule by changing its charge-to-mass ratio. In the second phase of the method, complex formation can be detected simply by monitoring the migration of the target molecule during electrophoresis. The off-rates of ligands detected will be long compared to the run time of the capillary electrophoresis phase. Any ligands that bind to the target molecule may be strong candidates for therapeutic lead compounds or diagnostic compounds. The CE separation phase facilitates the isolation and characterization of any binding ligands for subsequent testing for, e.g., therapeutic efficacy and pharmacokinetic properties. Thus, in one step a crude natural sample may be fractionated and screened for potential medicinal compounds. Using dye-conjugated molecules and laser-induced fluorescence, this method can detect ligand concentrations in the low nanomolar range in the crude sample, substantially lower than the micromolar concentration limit in most current natural product screens. The fractionated complex may be collected from the capillary or directly analyzed, e.g., off-line or by coupling the capillary to standard analytical devices such as a mass spectrometer.

Any molecule that is implicated in a disease process is a potential therapeutic molecular target. Furthermore, the potential target molecule may be any compound whose detection is desired for diagnosis of a specific condition. Additionally, other categories of target molecules can be contemplated. For example, in the agricultural arena the target could be a molecule representing an essential function of an insect pest.

Some examples of therapeutic target molecules are included in the following table:

| Molecular Target | Associated Disease(s) |
| --- | --- |
| HIV reverse transcriptase | AIDS |
| HIV protease | AIDS |
| Carbonic anhydrase | Glaucoma |
| Tubulin | Cancer |
| Thrombin | Blood clots |
| HMG-CoA reductase | High cholesterol |
| Elastase | Emphysema, Rh. arthritis |
| Cyclooxygenase | Inflammation |
| p56, p59 tyrosine kinases | Cancer |
| Topoisomerases | Cancer |

Other examples of appropriate molecular targets include DNA, RNA, ribosomes, cell membrane proteins, growth factors, cell messengers, telomerases, elastin, virulence factors, antibodies, replicases, other protein kinases, transcription factors, repair enzymes, stress proteins, uncharacterized disease-related genes and their RNA and protein products, uncharacterized disease-related regulatory DNA or RNA sequences, lectins, hormones, metabolic enzymes, proteases and toxins. The definition also includes any subcomponent of the listed molecules such as protein subunits, active peptide domains of therapeutic proteins, and active regions of small molecules. The molecule may be chemically, enzymatically or recombinantly altered, e.g., deglycosylated, to improve its electrophoretic properties or subjected to fluorophore or polyion addition to facilitate separation and/or detection.

Any pure or impure sample, e.g., a natural sample, that contains recombinant or non-recombinant complex biological material is considered an appropriate sample to be analyzed by the method of the invention. Natural samples include, but are not limited to, extracts of terrestrial and marine plants, cells from higher animals including humans, eubacteria, actinomycetes and other bacteria, microbial fermentation broths, both filamentous and non-filamentous fungi, protozoa, algae, archaebacteria, worms, insects, marine organisms, sponges, corals, crustaceans, viruses, phages, tissues, organs, blood, soil, sea water, fresh water, humus, detritus, manure, mud, and sewage.

Furthermore, "complex biological material" is intended to include any mixture of compounds that are potentially useful in a biological system, e.g., human, other mammalian or agricultural. For example, large chemical libraries are frequently generated by combinatorial chemistry to enable investigators to screen extremely large numbers of chemical compounds for potential therapeutic or diagnostic purposes. These libraries can be, in essence, modified biological scaffolds and could be screened advantageously by the method of the invention.

A typical CE system includes a separation capillary (coated or uncoated), which may or may not contain a sieving or interaction matrix, electrophoresis and collection buffers supplying the inlet and outlet end of the capillary, respectively, and a collection apparatus to transport separated sample components for further analysis. The particular conditions appropriate for a specific natural sample and specific target molecule can be determined by routine experimentation according to methods well known to those of ordinary skill in the art.

The conditions used will be determined mainly by the characteristics of the target molecule including its overall charge, structural stability, functional activity, and detection potential under various buffer and electrophoretic conditions. For example, some proteins such as tubulin are active within a narrow range of pH values (6.8–7.2). The use of buffers in this range dictates the overall charge on the protein and thus the polarity of injection. At near-neutral pH, tubulin carries a slight positive charge so that electrophoretic migration would occur from anode to cathode. Also, high ionic strength is required for some proteins such as tubulin to remain active, so gravity injection is preferred over electrokinetic injection because high salt content interferes with electrokinetic injection. In turn, the electric field would depend on the current produced by the buffer. Usually, a high electric field is desirable, although not so high as to generate negative effects from Joule heating. Longer total capillary lengths can be used to improve resolution. However, longer capillaries also increase the time of the experiment, which is detrimental to sample throughput. CE may also be carried out in capillaries in the form of open grooves or channels in a planar surface such as a fused silica or polymer microchip.

The migration of the tracked molecule is followed typically through the use of an on-column detector attached to a small window etched into the capillary. Alternatively, it is possible to scan the entire capillary or to perform a complete scan on individual peaks using a diode array spectrophotometer. Preferred detection methods are through the use of UV absorbance and laser-induced fluorescence. Chemiluminescence, refractive index, radionuclide, fluorescence polarization, NMR, mass spectrometry and electrochemical detection may also be used.

The detection variable for direct detection can be absorbance at 210 or 280 nm for most proteins and 260 nm for nucleic acids. Indirect detection uses laser-induced emission of mainly visible wavelengths from dye-labeled target molecules or competitor ligands. Examples of fluorescent dyes include fluorescein, rhodamine, Texas Red and ethidium bromide. It must be kept in mind, however, that these labels can influence the overall charge on the target molecule. Examples of UV sources and lasers include: deuterium, xenon and mercury lamps; argon, Ar/Kr, HeCd, HeNe, XeCl, KrF, nitrogen and solid state lasers. Some target molecules, such as DNA, may require a sieving matrix such as linear polyacrylamide for high resolution and identification of complex formation. Others, such as carbohydrates and small molecules, may require pre-capillary derivatization.

Electrophoretic migration time is proportional to the charge-to-mass ratio of the molecule. Binding of a charged or large ligand to a target molecule can be observed either by a change in the electrophoretic migration time of the target molecule or by a change in peak shape or area. As will be described in more detail below, binding of a charged biotin derivative to streptavidin resulted in a 23 second shift in the migration time of the complexed streptavidin compared to unbound streptavidin. In another example, binding of the natural product hirudin to the therapeutic target protein thrombin resulted in disappearance of the thrombin peak and appearance of a possible complex peak approximately 1 min. earlier. In another case, hirudin binding altered the mass, charge, and/or structure of the thrombin such that the complex was not detectable under the electrophoretic conditions used.

Binding of a small, uncharged ligand, as well as binding of charged ligands, can be detected through competitive binding assays. In this variation of the method, the target molecule is incubated with the natural sample, and, subsequently or separately, the target interacts with a known, charged ligand that produces an expected shift in the target migration. An inhibition or change in time of this shift indicates that the binding site of the known ligand is now occupied by another ligand from the natural sample.

For example, if a relatively weak binding, known, charged competitor ligand is present in excess in the electrophoresis running buffer, the target molecules would be interacting with the known ligand in equilibrium and would have changed the mobility of a target/known ligand complex when the target is tracked. Upon capillary electrophoresis of a target molecule/natural sample mixture, again in the presence of the known competitor in the running buffer, any small, neutral or differently charged ligands tightly bound to target molecules would prevent the binding of the known ligand, and a portion of the tracked target molecules would shift back to the migration position of the target in the absence of known ligand, thus identifying the presence of a "hit."

Alternatively, if the target molecule is difficult to track, the mobility of the known competitor ligand may be followed. In this case, the chosen known, competitor ligand (labeled or unlabeled) would be tight binding and would be added to the target/natural sample mixture in equimolar concentration to the target. Upon electrophoresis of the natural sample mixture, the competitor ligand would be tracked. The reappearance of unbound known, competitor ligand would mean that certain target molecules were now bound to a new ligand from the natural sample.

Any known, charged molecule that binds a target molecule and, upon binding, causes an alteration in the electrophoretic profile of either the target or itself is a suitable ligand for the competitive binding assay. Other examples of competitive ligands include the following molecules and their derivatives and analogs: peptides, oligonucleotides, small proteins, ions, metals, peptoids, carbamates, diversomers, polyamines and small pharmaceutical-like molecules.

Approximately a 5% –10% shift in migration time compared to an inert internal standard (e.g., mesityl oxide, myoglobin) is considered to be significant. Alternatively, a 10% or greater reduction in peak area is also significant. In addition, any change in peak shape, including peak broadening, peak skewing, or a new peak shoulder is a significant change in practicing the CE screening method of the invention for natural sample ligands.

Depending on the source of material, natural samples contain a variety of diverse compounds which may interfere with any screening method. These compounds fall into general categories such as polyphenols, polyphosphates, lipids, proteins, polysaccharides, sterols, vitamins, and small ions. Most compounds that commonly interfere with standard assays are either negatively-charged (polyphosphates) or neutrally-charged (polyphenols, lipids) molecules (Bull et al., Annual Rev. Microbiol. 46:219–252, 1992). Therefore, by providing a net positive charge on the molecule that is being tracked, the described method can be adjusted to eliminate most of these interfering species in the same step as the affinity reaction. There are a number of ways this can occur. First, the tracked molecule may already be positively charged under most buffer conditions. Second, the buffer conditions can be modified so that the net charge is positive. Of course, it is important that the target is still functional if a low pH is used. Third, a polycationic species can be attached to a target molecule by, for example, covalent attachment at sulfhydryl groups of proteins. If free sulfhydryl groups are not available, they may be engineered into the protein by recombinant DNA methodology. This capability is a major advantage of the method of the invention as it represents an effective way to eliminate a potentially large source of background interference without introducing additional steps, an important consideration for automating the process.

The natural sample may be one that is harvested from the environment and/or cultured under suitable environmental conditions (growth medium, temperature, humidity). Preferably, the harvested sample is simply diluted to the extent necessary to practice the method of the invention. However, if necessary, the sample material can be treated by any combination of standard processes used by those skilled in the field to prepare the sample for analysis. For example, the crude sample may be subjected to a preliminary treatment such as freeze-thawing, homogenization, sonication or microwave extraction to break down cell walls. A typical next step would be heat treatment (e.g., 50° C. at 10 min to inactivate destructive enzymes). Addition of non-specific protein to prevent destruction of the target by heat-resistant proteases may be performed. Extraction of cells or culture media with various solvents such as ethyl acetate, dimethylsulfoxide, ethanol, methanol, ether or water can be carried out, followed by filtration to remove particulate matter and/or high molecular weight compounds. The natural sample may also be fractionated by centrifugation, sequential extractions, high pressure liquid chromatography, thin layer chromatography, and/or countercurrent chromatography, followed by isolation of the fractions prior to treatment by the method of the invention. Finally, the sample may be diluted in aqueous or non-aqueous solution, which may contain salts and buffers such as sodium chloride, sodium citrate or Good's biological buffers. For most samples, the dilution step is required and preferably is the only treatment. However, dilution can also be performed as a final procedure after one or more of the preceding steps. A 1:20 (vol./vol.) dilution of the original natural sample is usually necessary to achieve reproducible results.

The method of the invention can be applied as a rapid, simple primary screening tool of natural samples for new therapeutic compounds. If a positive sample is obtained, there are a variety of ways to approach the isolation and characterization of the ligand(s). One method would be affinity chromatography, in which the ligand is first bound to a target, the ligand/target complex is isolated, and the ligand is later dissociated from the target and concentrated. Another method is to fractionate using standard extraction procedures and solvents of varying polarities followed by chromatography. The ligands, once isolated, can be subjected to standard structural determination procedures such as IR and NMR spectroscopy. The isolated ligands can also be tested for functional activity in cell-based and biochemical assays. A third method would be to interface the capillary with a mass spectrometer for direct structural analysis of the complex(es). This method is especially important for rapidly identifying and discarding previously isolated compounds (dereplication).

The preferred method of the invention is specific in that only high affinity compounds with tight binding give a positive signal. Multiple, weak binding ligands with high off-rates, which often plague standard affinity assays by giving false positive reactions, will not be observed. High resolution is also possible. Using laser-induced fluorescence, low nanomolar concentrations are detectable, which is a lower detection limit than most standard assays.

In an entirely solution-based affinity system, such as the system of the invention, contact is possible between all of the sample components and the target. Also, there is no solid-bound phase (as used in a standard ELISA test) that can destroy the physiological activity of protein targets in particular. Full automation and multiplexing of the method (using multiple capillaries and compound mixtures) is also possible. Very little sample is required (<5 μL for ten replicate runs) and very little background buffer as well (<5 mL for 50 runs), and a total analysis time of 10 min. per sample is typical.

The following examples are presented to illustrate the advantages of the present invention and to assist one of ordinary skill in making and using the same. These examples are not intended in any way otherwise to limit the scope of the disclosure.

EXAMPLE I

The method of the invention is based on the principle that the electrophoretic mobility of a therapeutic target molecule in a capillary can be altered upon binding a charged and/or large ligand. This principle can be used to identify binding compounds in complex natural samples upon capillary electrophoresis where the electrophoretic mobility of a target molecule is specifically affected by the mass and charge of a binding ligand. A reaction illustrating this principle is as follows (Chu et al., J. Med. Chem. 35:2915–2917, 1992):

|  | target therapeutic molecule | + | ligand in natural sample | = | complex |
|---|---|---|---|---|---|
| Mass | M |  | m |  | M + m |
| Net charge | Z |  | ±z |  | Z ± z |
| Electrophoretic mobility | $Z/M^\alpha$ |  |  |  | $(Z \pm z)/(M \pm m)^\alpha$ |

$\alpha$ = coefficient based on shape of complex

For identifying small, neutral ligands, the same principle can be applied using known, charged ligands in competitive binding reactions.

Figure 2A:
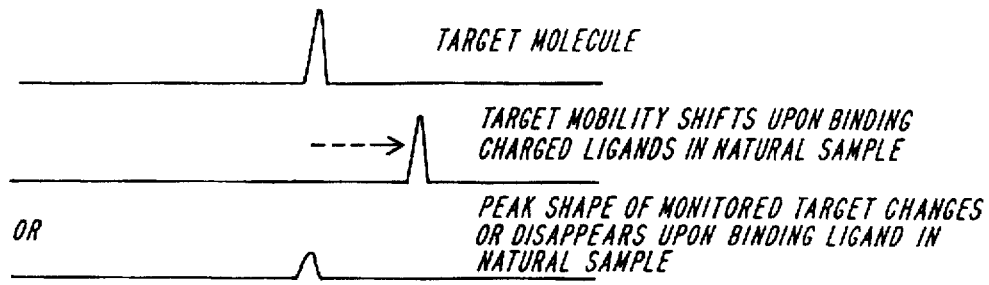
FIG. 2a shows one model for detecting direct binding in the method of the invention.

Application of this principle in the method of the invention leads to at least three separate models for isolating new ligands from natural samples. Referring to FIG. 2a, direct binding can be utilized for detecting charged ligands. The therapeutic target molecule is monitored, and the mobility of the target molecule shifts upon binding of charged ligands from the natural sample. Alternatively, the peak shape of the monitored target molecule can change or even disappear if the absorbance property of the complex is changed.

Figure 2B:
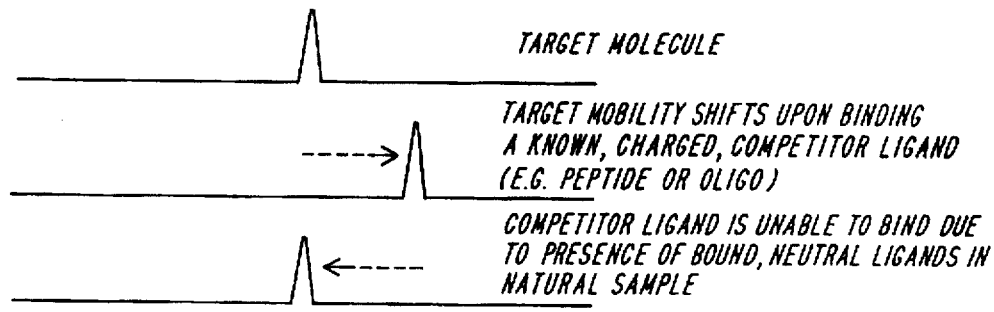
FIG. 2b shows another model for detecting direct binding in the method of the invention.

The model shown in FIG. 2b illustrates a method of detecting small, neutral ligands. In this model, the mobility of the target molecule is again monitored, and, as above, the mobility of the target shifts upon ligand binding, this time to a known, charged, competitor ligand (e.g., peptide, oligonucleotide, small molecule). However, if the target molecule is first incubated with the natural sample and then with the competitor ligand, the competitor ligand is unable to bind due to the presence of bound, neutral ligands from the natural sample. This method will also detect charged molecules if the shift in electrophoretic mobility is different from that of the shift upon binding of the known ligand.

Figure 2C:
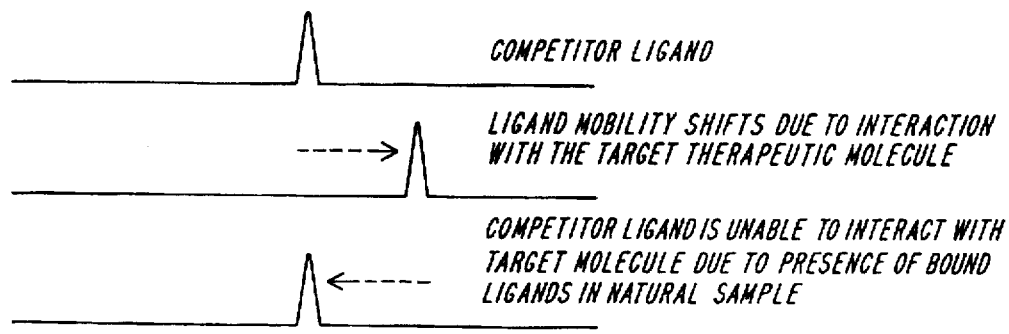
FIG. 2c shows another model for detecting direct binding in the method of the invention.
Figure 3A:
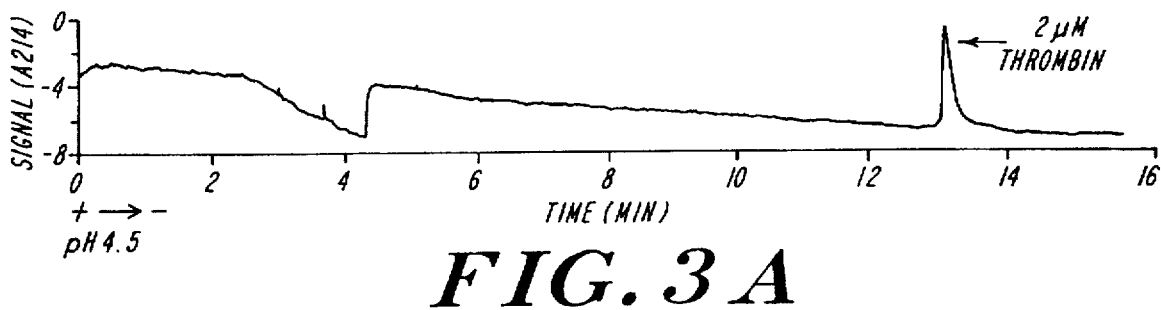
Figure 3B:
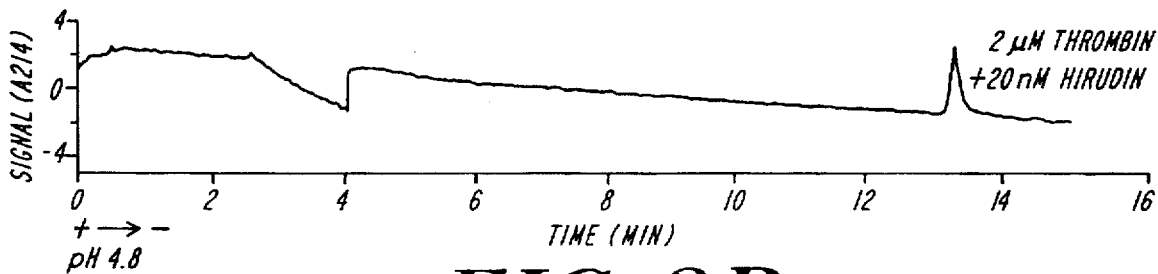
Figure 3C:
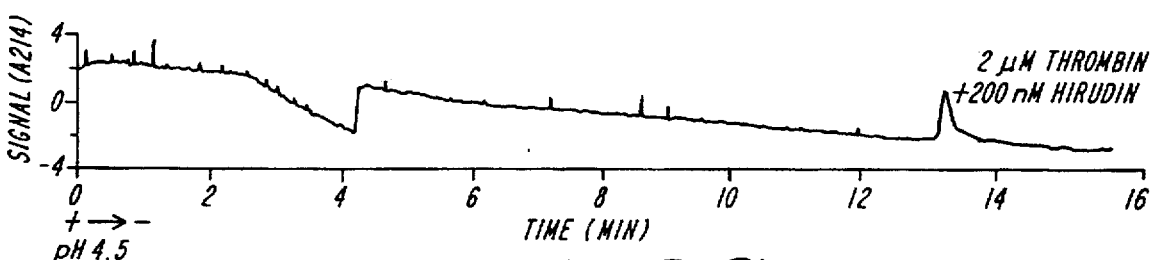
Figure 3D:
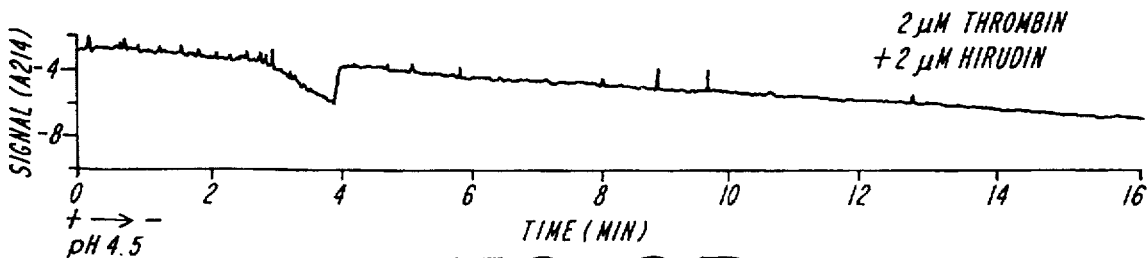
Figure 4A:
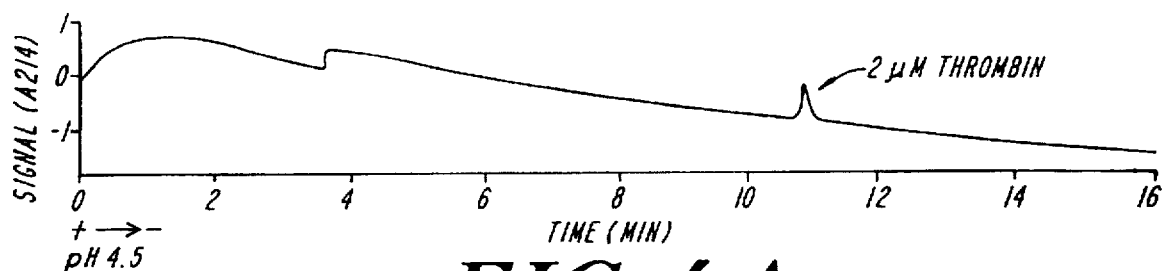
Figure 4B:
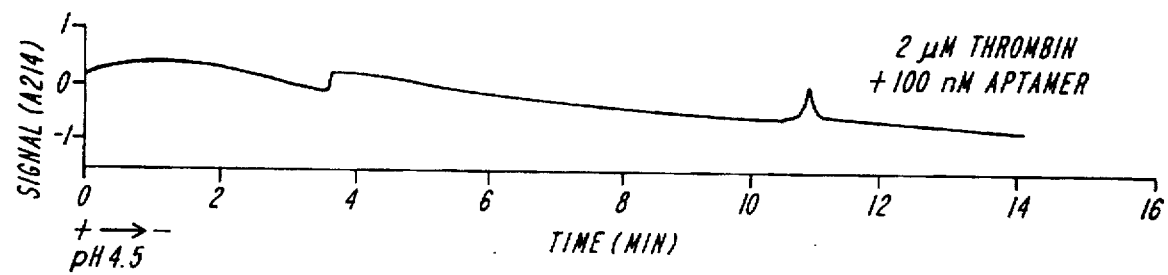
Figure 4C:
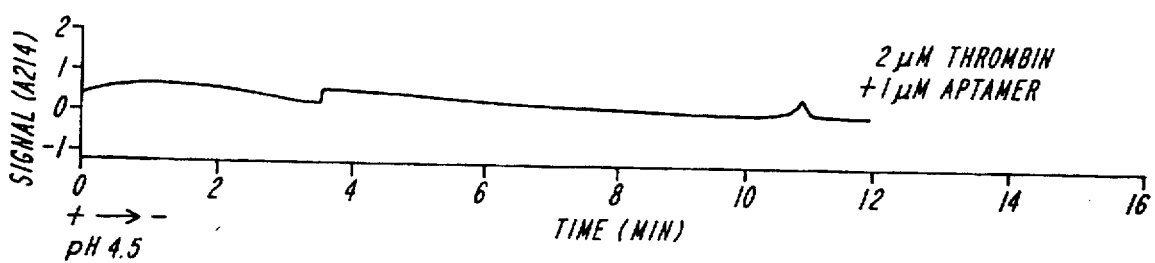
Figure 4D:
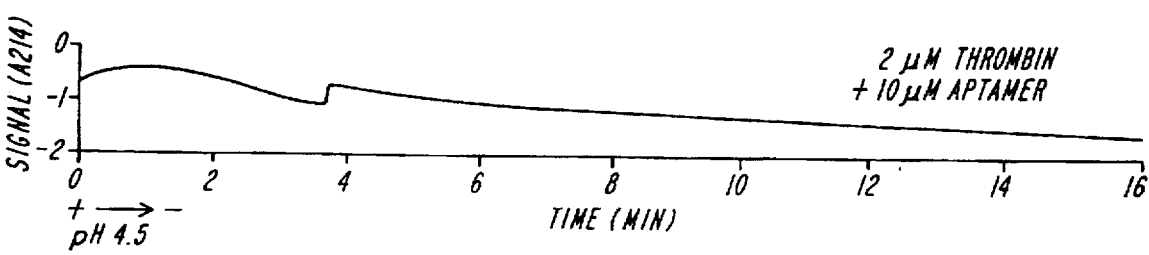
Figure 5A:
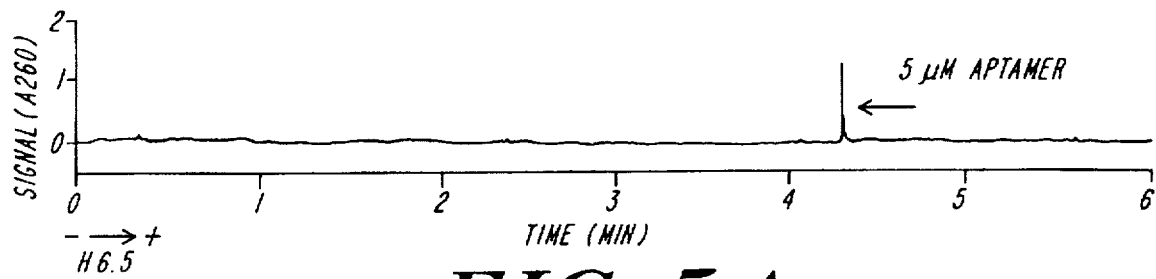
FIG. 5 shows capillary electrophoresis of thrombin in the presence of a thrombin-binding aptamer, with or without hirudin, as an example of the model shown in FIG. 2c.
Figure 5B:
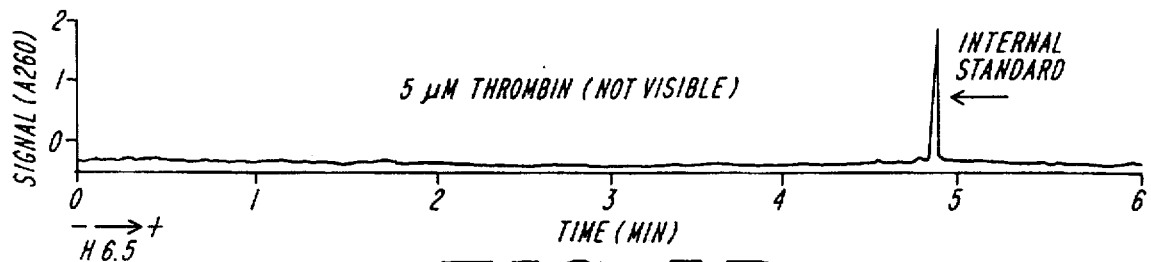
Figure 5C:
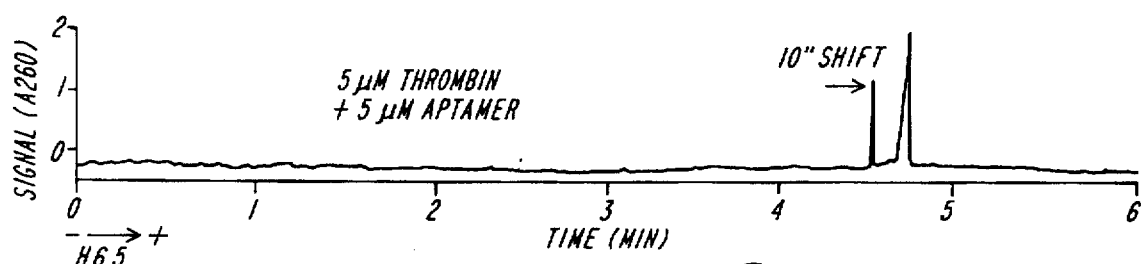
Figure 5D:
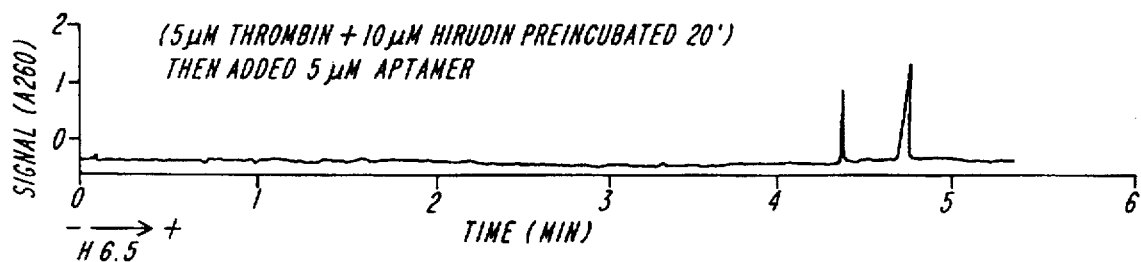

The third model, shown in FIG. 2c, illustrates detecting either neutral or charged ligands. In this model, competitive binding with a known charged ligand is again used, but the mobility of the competitive ligand is monitored. This would be advantageous if the target molecule is difficult to observe directly. Upon CE in the presence of the target but the absence of a natural sample, ligand mobility shifts due to interaction with the target therapeutic molecule. However, in the presence of bound ligands in the natural sample, the competitor ligand is unable to interact with the target molecule, and its mobility is unchanged.

EXAMPLE II

As an example of the model shown in FIG. 2a, the interaction of the blood clotting protein thrombin and its natural inhibitor hirudin was monitored. Referring to FIG. 3, panel A, CE of thrombin in a polyvinyl alcohol-coated capillary in the absence of hirudin produces a well-formed peak. As shown in FIG. 3, panels B–D, however, the thrombin peak disappears in the presence of increasing concentrations of the natural inhibitor hirudin. Presumably, hirudin binding alters the mass, charge, and/or structure of the thrombin so that the complex is not detectable under these conditions. The conditions were: background buffer:ε-amino-n-caproic acid, pH 4.5; electric field: 400 V/cm; injection time: 30" by gravity at the anode; detection: 214 nm. No new peaks were observed in the opposite polarity under the same buffer conditions.

Another example of the model shown in FIG. 2a is given in FIG. 4. Under identical electrophoretic conditions as the thrombin/hirudin interaction, increasing concentrations of the single-stranded, thrombin-binding aptamer 5'-GGTTGGTGTGGTTGG-3' also results in the disappearance of the thrombin peak. (Refer to FIG. 4, panels A–D.) Again, complex formation is not detectable under these conditions. The thrombin peak was unchanged in the presence of equivalent concentrations of a random oligonucleotide.

The experiment shown in FIG. 5 is an example of the model of FIG. 2c, where a competing ligand (thrombin aptamer) is monitored in the presence of a natural product ligand (hirudin) and therapeutic target protein (thrombin). As with hirudin, the thrombin aptamer binds tightly to the anion-binding site of thrombin. In this experiment, the aptamer mobility is monitored in the presence of hirudin-bound or free thrombin. The mobility of the aptamer is slower in the presence of free thrombin (FIG. 5, panel C), but not when the thrombin is complexed to hirudin (FIG. 5 panel D). This suggests that the interaction between thrombin and the aptamer could not occur in the presence of bound hirudin, resulting in no aptamer peak shift. Electrophoretic conditions were as before, except that 2-[(2-amino-2-oxoethyl)amino] ethane sulfonic acid (ACES), pH 6.5 was the background buffer and sample injection was at the cathode end.

EXAMPLE III

Culture broth from the actinomycete bacteria *Streptomyces coelicolor* and the streptavidin/biotin system were used to demonstrate the principle of the method of the invention in a "natural sample" environment. Actinomycetes, particularly the streptomycetes, are a tremendous source of therapeutic compounds including anticancers, immunomodulators, antifungals, antihelminthics, and 70% of all antibiotics on the market. *S. coelicolor* is genetically and biologically the best understood member of this important group of organisms. *S. coelicolor* broth was chosen because streptavidin peak shape and migration time are not significantly affected by the broth, which indicates that very little streptavidin-binding material is present. This provides a convenient means to study streptavidin/biotin complex formation in the presence of a complex natural sample without interference from other compounds in the broth. Streptavidin and biotin form an extremely tight complex with a dissociation constant of $4\times10^{-14}$M.

CE was employed to analyze various combinations of cell-free culture broth, streptavidin, and biotin. The capillary dimensions were 75 µm in inner diameter with a total length of 63 cm and 49 cm to the detection window. The running conditions were 200 volts per centimeter in 20 mM TAPS/Tris (pH 8.5) with absorbance monitored at 280 nm. Without culture broth, the streptavidin/biotin complex demonstrated a 23 second longer migration time than streptavidin alone, indicating binding of the negatively-charged biotin molecules. This 23 second shift in peak time was also demonstrated in the presence of a 1:10 dilution of *S. coelicolor* culture broth. The biotin was then titrated to decreasing concentrations to determine the minimal detectable concentration of the ligand in the broth. At 820 nM biotin, a slight streptavidin peak shift was still observable. This corresponds to a minimal effective detection limit of 8.2 µM biotin because the broth sample was originally diluted tenfold.

The minimal detection limit 8.2 µM observed in this example is equivalent to or better than the minimal limit in current natural product screens and may be improved at least 10,000-fold using dye-conjugated target molecules and laser-induced fluorescence detection. Thus, detection levels for binding compounds in natural samples may be in the picomolar range, far below that of current natural product screens.

EXAMPLE IV

Figure 6:
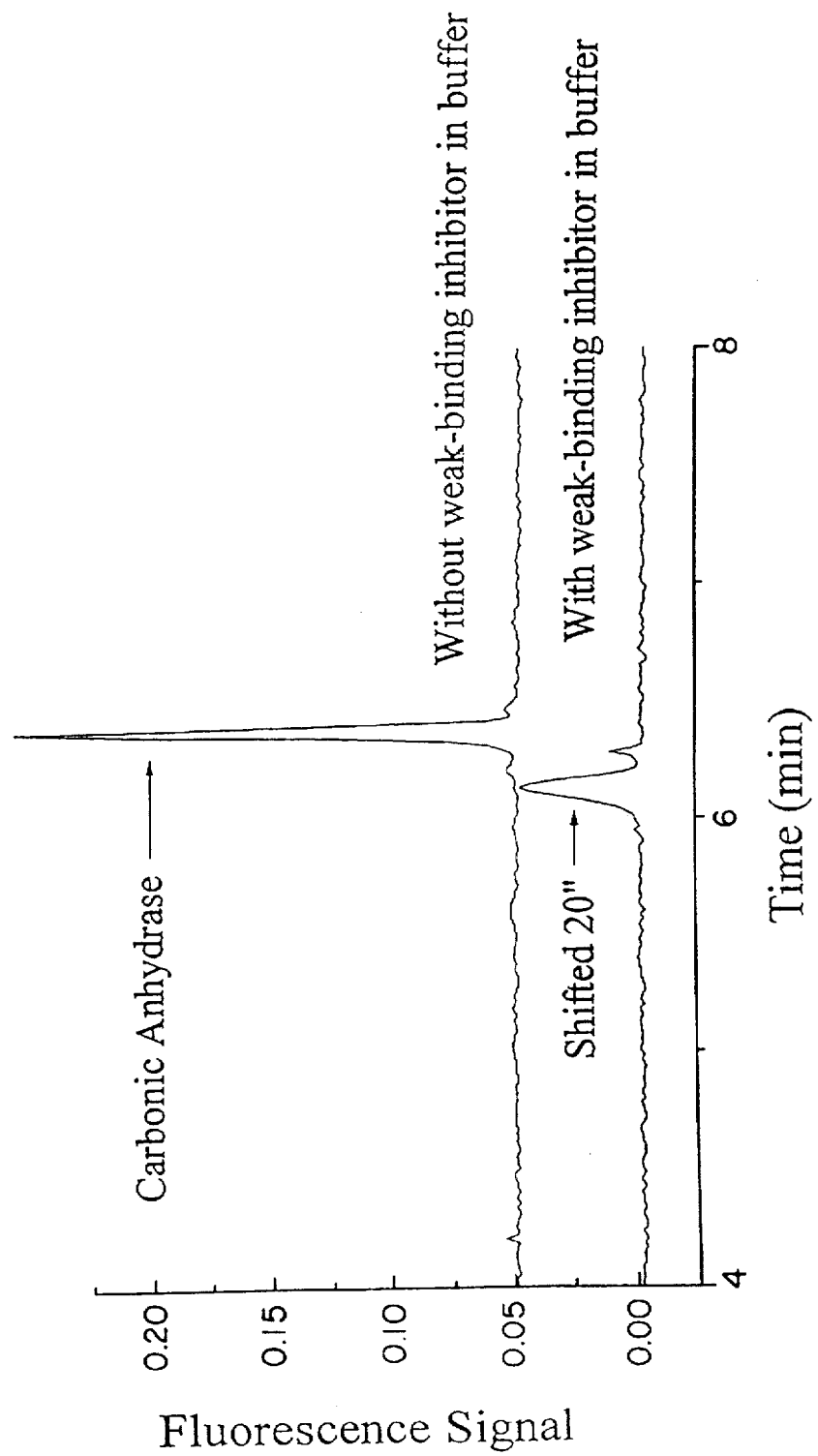
FIG. 6 shows capillary electrophoresis of carbonic anhydrase in the presence and absence of a weak-binding, negatively-charged inhibitor.

To demonstrate the low detection levels possible with the method of the invention, the therapeutic target enzyme human carbonic anhydrase II (HCAII) was fluorescently labelled by covalent attachment of fluorescein at the free sulfhydryl group of the enzyme's single cysteine. Low nanomolar concentrations of the dye-labelled protein showed a single peak when run on CE and monitored using laser-induced fluorescence (FIG. 6, upper plot). When a weak-binding, negatively-charged HCAII inhibitor was included in the background buffer, the HCAII peak velocity was 20" faster (FIG. 6, lower plot). This occurred because interaction of the negatively-charged inhibitor with HCAII resulted in a greater negative charge on the migrating HCAII molecules, causing a faster migration of the enzyme in the direction of the anode.

Figure 7:
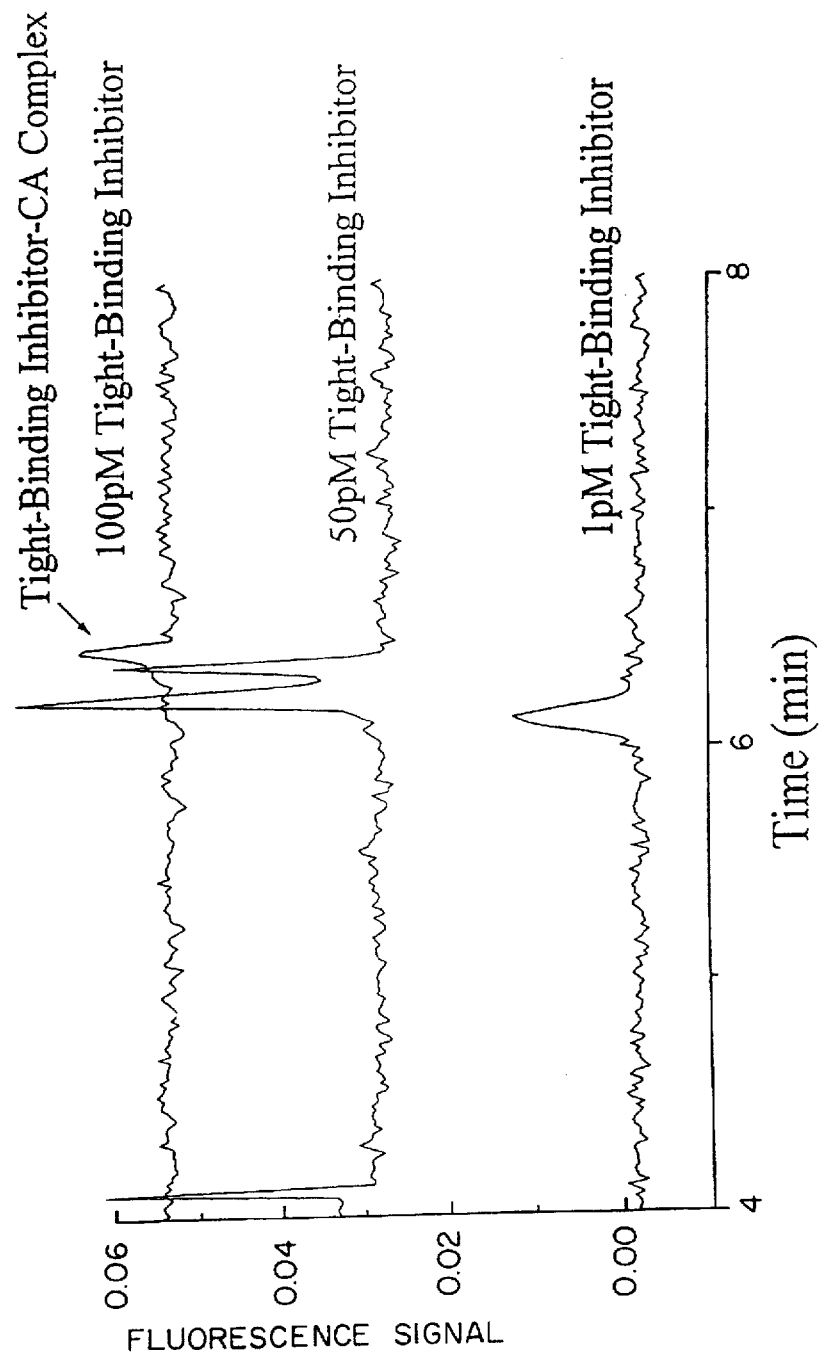
FIG. 7 shows capillary electrophoresis of carbonic anhydrase in the presence of a weak-binding, negatively-charged inhibitor and different concentrations of a tight-binding, neutrally-charged inhibitor.

In FIG. 7, the HCAII was pre-incubated with increasing amounts of the tight-binding, neutrally-charged inhibitor, which competes with the weak-binding inhibitor for the same site on the enzyme. All runs were performed in the presence of 1 µM weak-binding inhibitor, as in FIG. 6. In the lower plot, 1 µM of the tight-binding inhibitor had no effect on the migration of HCAII, which is still shifted by the bound negatively-charged inhibitor. With 100 pM of the tight-binding, neutrally-charged inhibitor present (FIG. 7, upper plot), however, the peak shift was inhibited nearly completely. In this case, the weak-binding inhibitor was unable to interact with HCAII due to the presence of the tight-binding inhibitor. As can be seen in FIG. 7, middle plot, at 50 pM the tight-binding inhibitor was not at saturating concentrations so both tight-binding, neutrally-charged-complexed HCAII and weak-binding, negatively-charged-shifted HCAII are seen.

This experiment was repeated in the presence of several inert natural samples with identical results. Thus, this example demonstrates that by combining laser-induced fluorescence with affinity capillary electrophoresis, picomolar levels of tight-binding inhibitors can be detected. This is well below the minimal detection limits of current natural sample screens.

The conditions were: background buffer: 100 mM CAPS [(3-[cyclohexylamino]-1-propanesulfonic acid)], 100 mM AMPD [2-amino-2-methyl-1,3-propanediol], pH 9.7; electric field: 550 V/cm; injection: 5" by pressure; excitation wavelength: 488 nm, emission wavelength: 522 nm.

EXAMPLE V

Fifty marine samples and seventeen actinomycete (e.g., Streptomyces) samples were tested in coated capillaries for their effect on the electrophoretic profiles of several therapeutic target proteins. The marine samples were prepared by extraction with DMSO and tested at final dilution of 1:20 (0.5 mg/mL). The actinomycete samples were filtered culture broths diluted 1:20. The actinomycete samples showed no effect on the mobility or peak shape of two exemplary target proteins, carbonic anhydrase and tubulin. However, several of the marine samples showed a positive effect on either the peak profile or electrophoretic migration time of thrombin (12/50) and carbonic anhydrase (2/50).

Figure 8A:
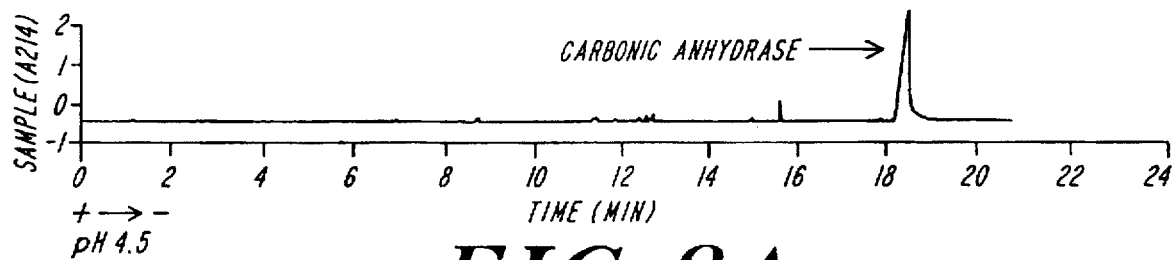
FIG. 8 shows capillary electrophoresis of carbonic anhydrase in the presence and absence of a marine sample that caused no difference in carbonic anhydrase mobility.
Figure 8B:
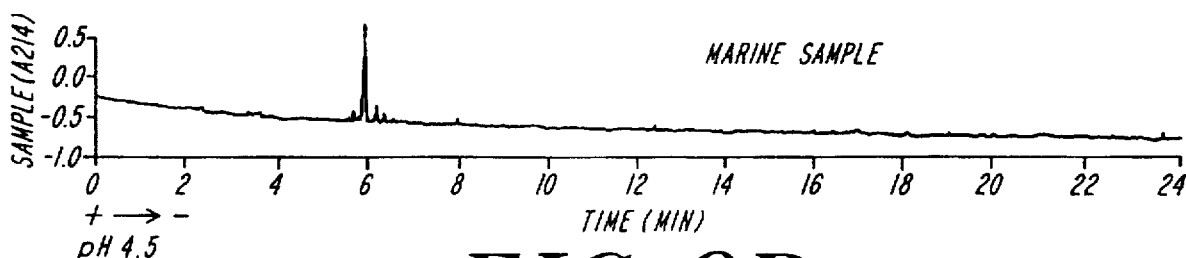
Figure 8C:
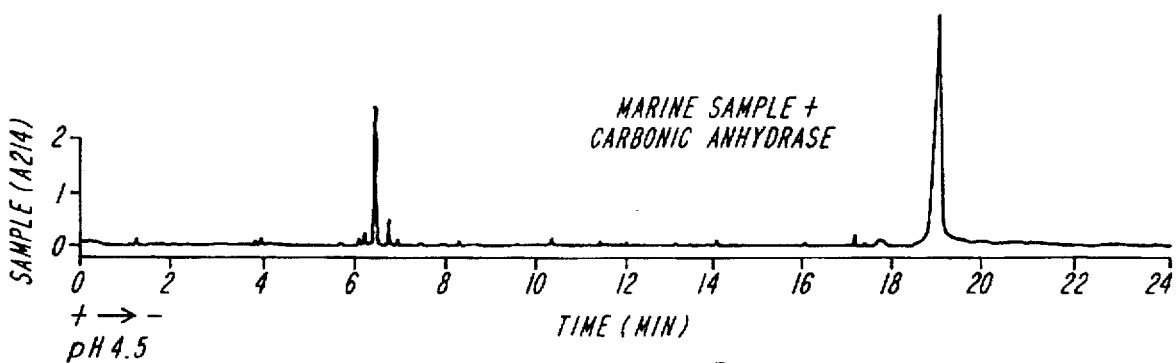
Figure 9A:
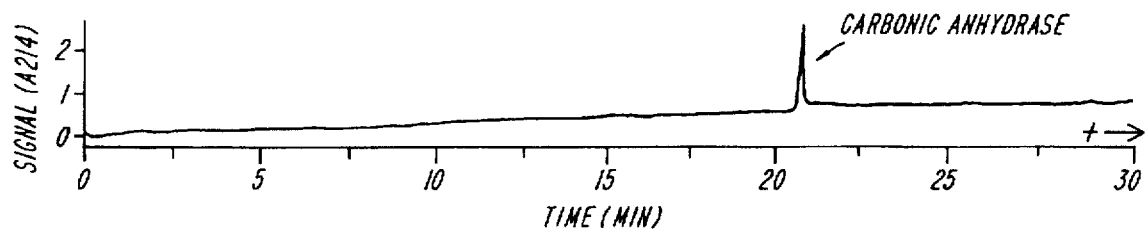
FIG. 9 shows capillary electrophoresis of carbonic anhydrase in the presence and absence of a marine sample that produced a change in carbonic anhydrase mobility.
Figure 9B:
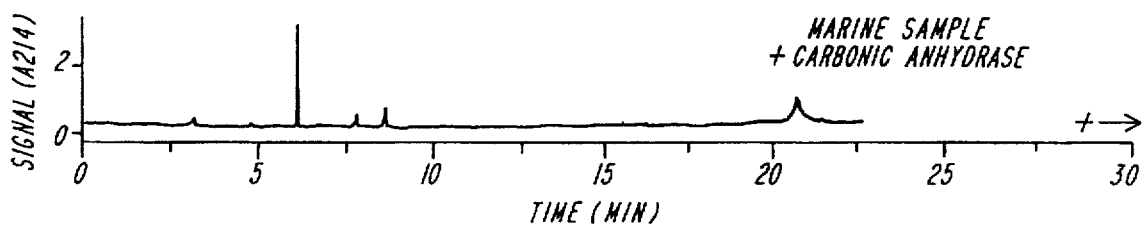
Figure 9C:
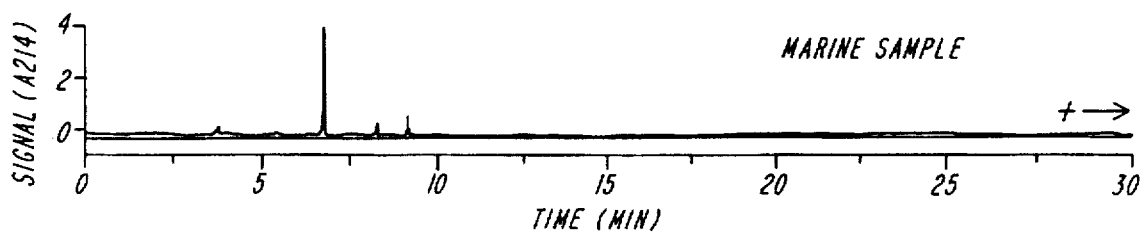
Figure 9D:
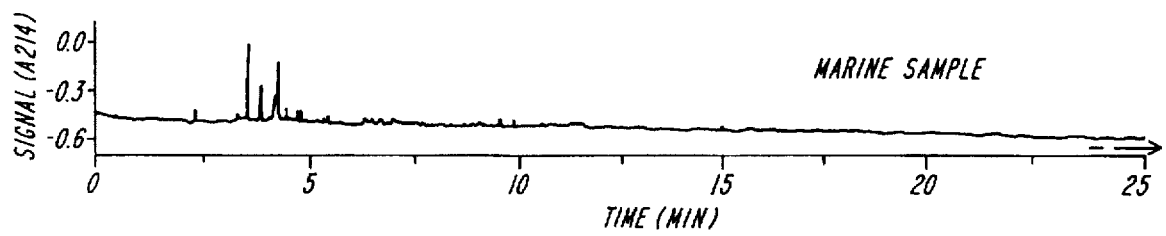
Figure 9E:
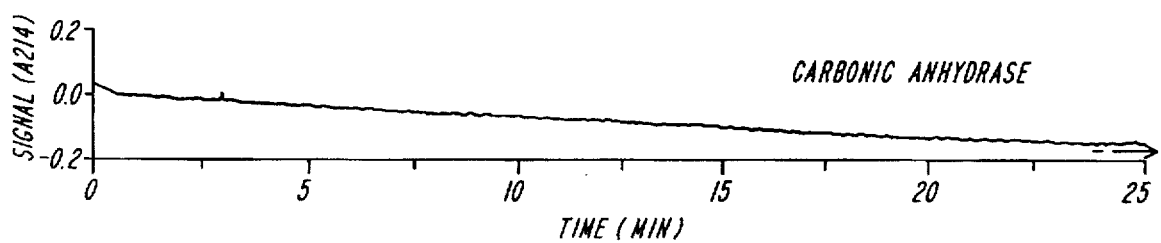
Figure 9F:
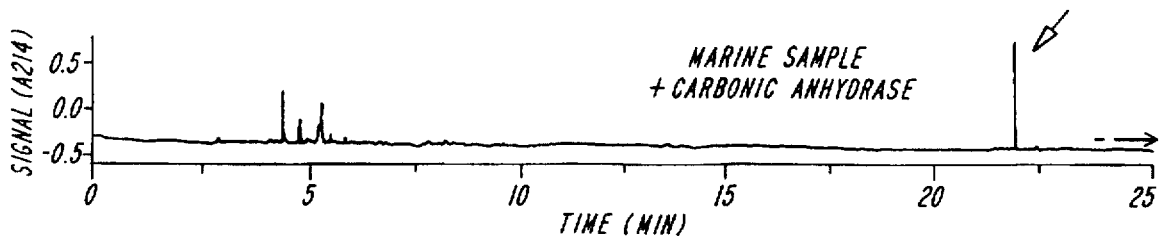
Figure 10A:
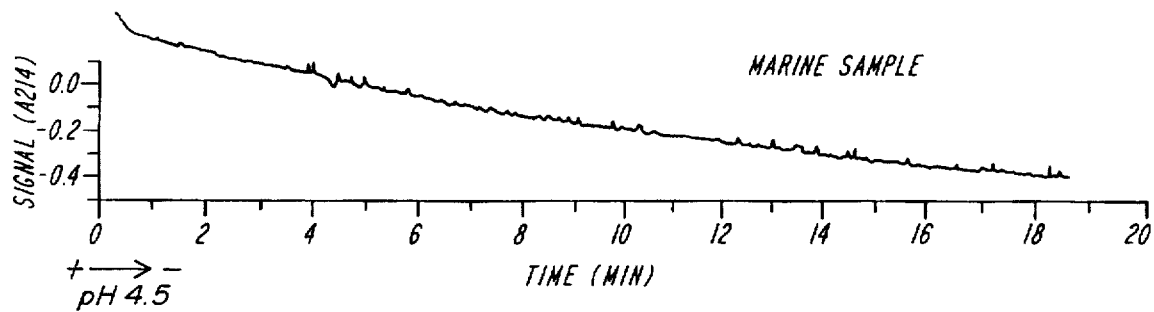
FIG. 10 shows capillary electrophoresis of thrombin in the presence and absence of a marine sample that produced a change in thrombin mobility.
Figure 10B:
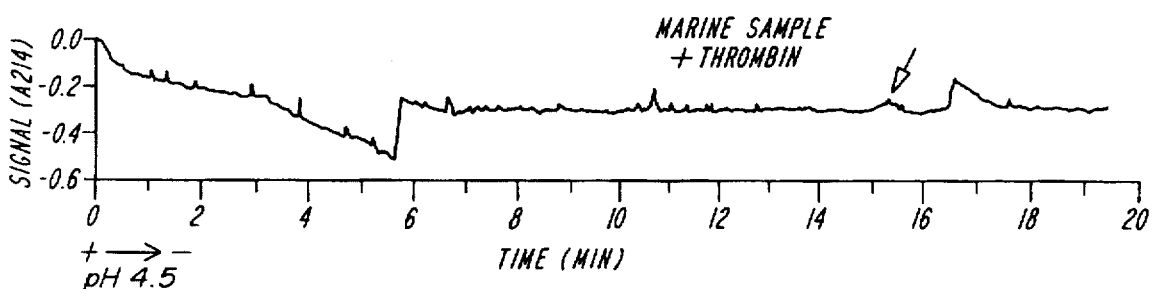
Figure 10C:
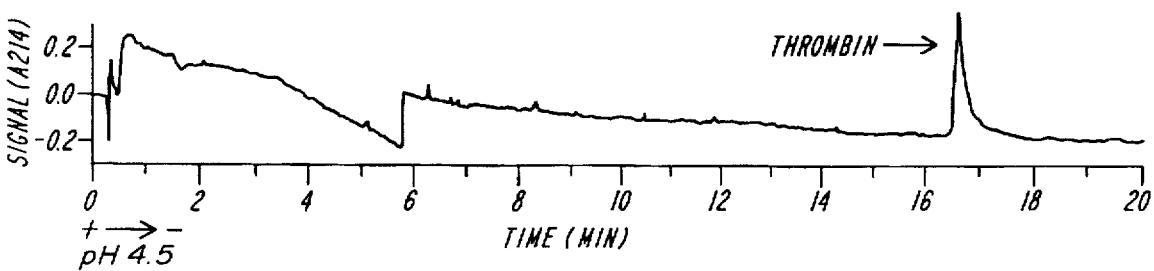

The electrophoretic profiles shown in FIGS. 8–10 are examples of specific experiments. Referring to FIG. 8, in most cases, the addition of a diluted (1:20) marine sample does not appreciably alter the electrophoretic profile of the target therapeutic protein carbonic anhydrase, nor is the profile of the marine sample itself altered. The electrophoretic conditions were: background buffer: ε-amino-n-caproic acid, pH 4.5; electric field: 400 V/cm; injection time: 30" by gravity at the anode; detection: 214 nm.

Referring to FIG. 9, one marine sample produced a decrease in the carbonic anhydrase peak (panels A–C) and appearance of a new peak (panels D–F), which was observed when the mixture was run in the opposite polarity (arrowhead in bottom panel F). Since the migration of the new peak is towards the anode, it appears as if there is an overall negative charge for the possible complex.

In another experiment, as shown in FIG. 10, one marine sample produced a decrease in the thrombin peak and a new peak (arrowhead in panel B) that may indicate a complex of thrombin with an unknown, positively-charged ligand.

EXAMPLE VI

Although twelve of the marine samples altered the thrombin profile in CE, only two of these samples demonstrated anti-thrombin activity in a standard coagulation test. There are several possible explanations for this phenomenon. For one, thrombin activity could actually be inhibited, but other serine proteases that promote coagulation could be present in the natural sample. Another possibility is that components in the coagulation assay inhibit any thrombin-binding ligands. Alternatively, some thrombin may be bound and inhibited, but there could be enough free thrombin for coagulation to occur. Other explanations are that the thrombin profile is altered in CE due to reasons other than binding such as salt or proteases present in the natural sample, or an inactive region of thrombin is bound by the ligand.

Five of the marine extracts that altered the thrombin profile in CE but did not inhibit coagulation time were tested further. The samples were separated into aqueous and organic phases, dried, and resuspended at a ten-fold higher concentration in DMSO. These fractionation and concentration steps uncovered anticoagulant activity in the aqueous phase of two of the samples, where it had previously been unobserved. This shows that the method of the invention is a superior method for primary screening of natural samples.

EXAMPLE VII

Figure 11A:
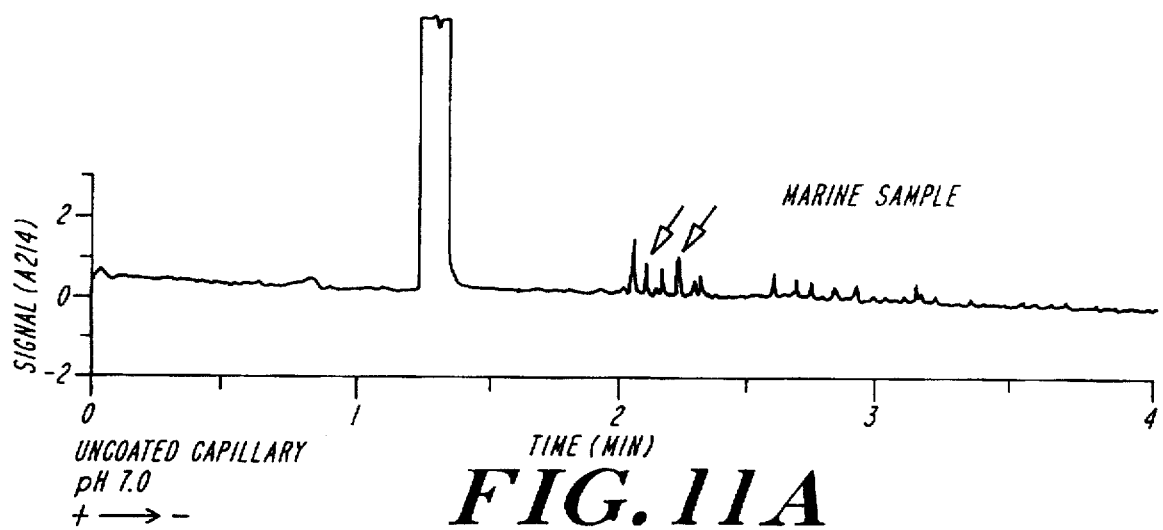
FIG. 11 shows capillary electrophoresis of samples such as those of FIG. 9 under different electrophoretic conditions, as an example of subtractive analysis.
Figure 11B:
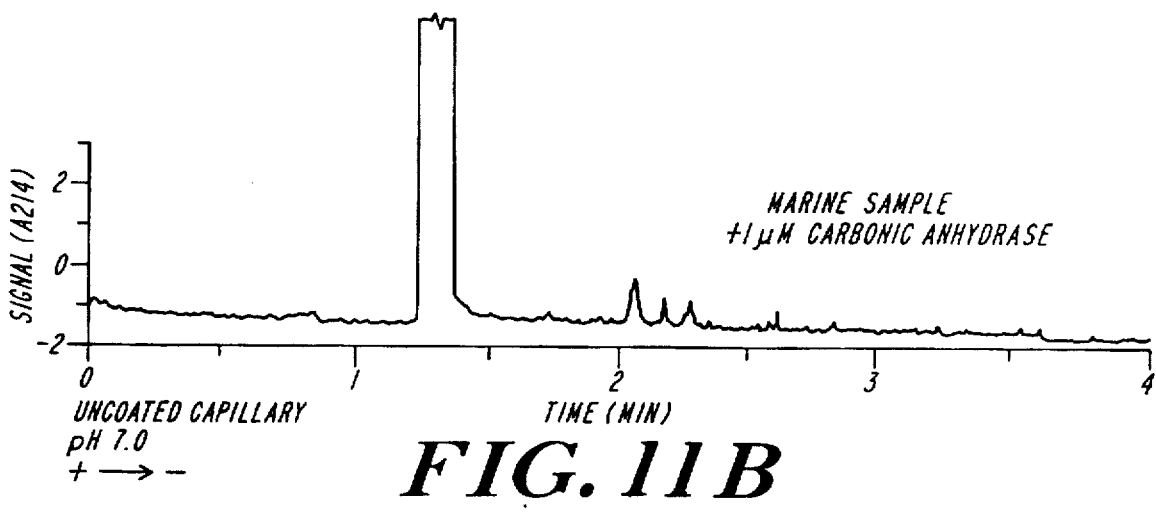
Figure 11C:
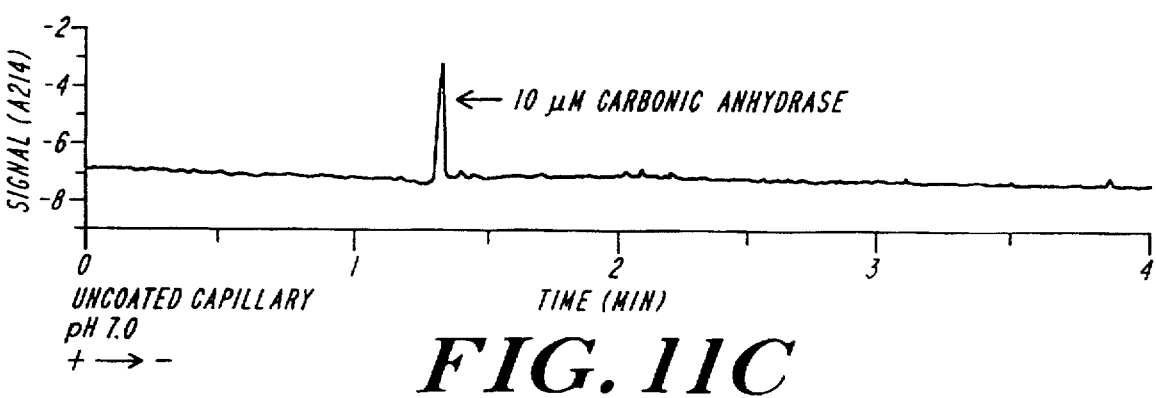

Binding ligands may also be identified by subtractive analysis. One marine sample that altered the profile of carbonic anhydrase in a coated capillary was further examined in an uncoated capillary. Due to electroosmotic flow, an uncoated capillary will reveal all UV-active compounds, charged and neutral, in a single run. The run conditions for this experiment were: background buffer: ACES, pH 7.0; electric field: 400 V/cm; injection time: 30" by gravity at the anode; detection: 214 nm. Referring to FIG. 11, it can be seen that the complex profile of the natural sample (panel A) changed upon pre-incubation with 1 μM carbonic anhydrase (panel B). Specifically, a few peaks disappeared (arrowheads in panel A), suggesting that CE can be used to directly identify interacting ligands in a crude sample. Interesting peaks may be isolated directly from the capillary or run into a mass spectrometer for further analysis.

Other embodiments

The described method can be developed into a system for rapidly screening large numbers of samples (high throughput screening) in four basic ways. First, it is currently possible to construct a simultaneous multicapillary system containing up to 96 parallel capillaries. In the future, it is probable that the number of capillaries monitored simultaneously will be increased further. Typically, a single laser beam source is split into numerous beams for monitoring the individual capillaries. A second method incorporates more than one therapeutic target per capillary so that a single natural sample may be simultaneously screened for compounds that bind different targets. This requires the selection of targets that have different absorbance/emission properties or different electrophoretic migration times. For example, each target could be conjugated to a different fluorescent dye. Targets must be selected so that, when mixed, they are stable, detectable, and active in the same running buffer. Third, natural samples may be mixed prior to screening. Up to five samples per capillary may be analyzed in this manner. After a positive reaction is obtained, deconvolution can be performed to identify the active sample(s). Although sample mixing increases throughput, it also dilutes potentially active compounds, making this the least desirable method for multiplexing. The final method for increasing throughput is to create capillaries on, e.g., fused silica microchips. In this case, many capillaries may be present on one microchip and, if short (two cm) capillary lengths are used, run times would be much faster. The microchip format also allows for the possibility of two-dimensional analysis where, for example, CE can be combined with an assay, such as a bioassay, of the identified ligand.

The described method may also be adapted to identify weak binding ligands in natural samples. This can be achieved by introducing the diluted natural samples or target in the running buffer, where rapid binding and dissociation of the target and ligands during the course of the run can be observed through altered mobility of the target or a competing ligand. This application would be useful for isolating weak-binding lead compounds that can later be modified for higher activity.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A method of screening complex biological material for previously unidentified ligands of a selected target, said method comprising, in the order given, the steps of:
   (1) providing a sample of complex biological material;
   (2) combining said sample of complex biological material with said selected target to form a sample/target mixture;
   (3) injecting an aliquot of said sample/target mixture from step (2) into an apparatus for capillary electrophoresis without sieving matrix;
   (4) subjecting said aliquot of said sample/target mixture to capillary electrophoresis without sieving matrix;
   (5) tracking the migration of said target upon said capillary electrophoresis;
   (6) determining whether the migration pattern of said target from step (5) indicates the presence of a candidate unidentified ligand in said sample of complex biological material;
   (7) isolating said candidate compound from said complex biological material; and
   (8) determining whether said isolated compound has not been previously identified as interacting with said target.

2. The method of claim 1, wherein said step (6) comprises:
   comparing the migration of said target to a reference standard comprising the migration time for an aliquot of said target alone to reach a detection point in said capillary electrophoresis apparatus.

3. The method of claim 1, wherein said step (6) comprises:
   comparing the migration pattern of said target to a reference standard comprising the migration pattern of an aliquot of said target alone.

4. A method of screening complex biological material for previously unidentified ligands of a selected target, said method comprising, in the order given, the steps of:
   (1) providing a first sample of complex biological material;
   (2) injecting said first sample of complex biological material into an apparatus for capillary electrophoresis without sieving matrix;
   (3) subjecting said first sample of complex biological material to capillary electrophoresis without sieving matrix;
   (4) following said capillary electrophoresis of said first sample, using a general detection method to detect the presence of compounds originating from said first sample of complex biological material and to produce a first detection pattern of compounds detected;
   (5) providing a second sample of said complex biological material;
   (6) combining said second sample of complex biological material with said target to form a sample/target mixture;
   (7) injecting an aliquot of said sample/target mixture into said apparatus for capillary electrophoresis without sieving matrix;
   (8) subjecting said aliquot of said sample/target mixture to capillary electrophoresis without sieving matrix;
   (9) following said capillary electrophoresis of said aliquot of said sample/target mixture, using said general detection method to detect the presence of compounds originating from said sample/target mixture and to produce a second detection pattern of compounds detected;
   (10) comparing said first detection pattern to said second detection pattern to look for any compound represented in said first detection pattern that is not represented in said second detection pattern;
   (11) isolating any compound originating from said complex biological material that is represented in said first detection pattern but is not represented in said second detection pattern; and
   (12) determining whether said isolated compound has not been previously identified as interacting with said target.

5. The method according to claim 1 or claim 4, further comprising testing said isolated compound for therapeutic efficacy or pharmokinetic properties against said target.

6. A method of screening complex biological material for candidate, unidentified ligands of a selected target said method, comprising, in the order given, the steps of:
   (1) providing a sample of complex biological material;
   (2) combining said sample of complex biological material with said selected target to form a first, sample/target mixture;
   (3) subsequently, combining said first mixture with a known, charged ligand of said target, to form a second, sample/target/known ligand mixture;
   (4) injecting an aliquot of said second mixture into an apparatus for capillary electrophoresis without sieving matrix;
   (5) subjecting said aliquot of said second mixture to capillary electrophoresis without sieving matrix;
   (6) tracking the migration of said known ligand upon said capillary electrophoresis; and
   (7) determining whether the migration pattern of said known ligand from step (6), when compared to a reference standard comprising the migration pattern of said known ligand in the presence of said target and the absence of said complex biological material, indicates the presence of a candidate unidentified ligand of said target, in said sample of complex biological material.

7. The method of claim 6 further comprising:
   isolating said candidate unidentified ligand of said target, whose presence has been indicated in step (7), from said complex biological material;
   determining whether said isolated compound has not been previously identified as interacting with said target; and
   testing said isolated compound for therapeutic efficacy or pharmokinetic properties against said target.

8. The method of claim 6 wherein said known ligand is tight-binding.

9. A method of screening complex biological material for candidate, unidentified ligands of a selected target, said method comprising, in the order given, the steps of:
   (1) providing a sample of complex biological material;
   (2) combining said sample of complex biological material with said selected target to form a sample/target mixture;
   (3) injecting an aliquot of said sample/target mixture into an apparatus for capillary electrophoresis without sieving matrix;

(4) subjecting said aliquot to capillary electrophoresis without sieving matrix, wherein a running buffer used to carry out said capillary electrophoresis comprises a known, charged ligand of said target;

(5) tracking the migration of said target in said aliquot, upon said capillary electrophoresis; and (6) determining whether the migration pattern of said target from step (5), when compared to a reference standard comprising the migration pattern of said target in the presence of said known, charged ligand in said running buffer and the absence of said complex biological material, indicates the presence of a candidate unidentified ligand of said target in said sample of complex biological material.

10. The method of claim 9 further comprising:

isolating said candidate unidentified ligand of said target, whose presence has been indicated in said step (6), from said complex biological material;

determining whether said isolated compound has not been previously identified as interacting with said target; and testing said isolated compound for therapeutic efficacy or pharmokinetic properties against said target.

11. The method of claim 9 wherein said known ligand is weak-binding.

12. The method of claim 1, 4, 6, or 9, wherein said apparatus for capillary electrophoresis without sieving matrix comprises multiple capillaries.

13. The method of claim 1, 4, 6, or 9, wherein said apparatus for capillary electrophoresis without sieving matrix comprises multiple channels on a planar microchip.

14. The method of claim 1, 4, 6, or 9, wherein, in said step of combining target with sample, said sample is combined with more than one target.

15. The method of claim 1, 4, 6, or 9, wherein the migration of said tracked molecule is monitored by detection of UV absorbance.

16. The method of claim 1, 4, 6, or 9, wherein the migration of said tracked molecule is monitored by detection of laser-induced fluorescence.

17. The method of claim 1, 4, 6, or 9, wherein, in said providing step, said sample comprises complex biological material from more than one source.

18. The method of claim 1, 4, 6, or 9, wherein said complex biological material has been subjected to at least one pretreatment step prior to said providing step, said at least one pretreatment being freeze-thawing, homogenization, sonication, microwave extraction, heating, solvent extraction, filtration, fractionation, or dilution.

19. The method of claim 1, 4, 6, or 9, wherein said apparatus for capillary electrophoresis without sieving matrix is coupled directly to an analytical device.

20. The method of claim 19 wherein said analytical device is a mass spectrometer.

21. The method of claim 13 wherein said planar chip is configured for two-dimensional analysis.

22. The method of claim 1, 4, 6, or 9, wherein said complex biological material is selected from the group consisting of extracts of terrestrial plants; extracts of marine plants; extracts of marine organisms; microbial broths; and microbial extracts.

23. The method of claim 1, 4, 6, or 9, wherein said complex biological material is a combinatorial library.

24. The method of claim 1, 4, 6, or 9, wherein said target is selected from the group consisting of HIV reverse transcriptase, HIV protease, human thrombin, protein kinases and active peptide domains of therapeutic proteins.

25. The method of claim 4 or claim 9, wherein said known ligand is selected from the group consisting of peptides oligonucleotides, small proteins, ions, metals, peptoids, carbamates, polyamines and charged small molecules.

26. The method of claim 1, 4, 6, or 9, wherein, in said tracking step, said tracked molecule has a net positive charge.

* * * * *

UNITED STATES PATENT AND TRADEMARK OFFICE
CERTIFICATE OF CORRECTION

PATENT NO : 5,783,397
DATED : July 21, 1998
INVENTOR(S): Dallas E. Hughes, et al.

It is certified that error appears in the above-identified patent and that said Letters Patent is hereby corrected as shown below:

Column 12, line 54, "1 $\mu$M" should read --1 pM--.

Column 18, line 31, claim 25, "peptides oligonucleotides," should read --peptides, oligonucleotides,--.

Signed and Sealed this

Sixteenth Day of November, 1999

Attest:

Q. TODD DICKINSON

Attesting Officer

Acting Commissioner of Patents and Trademarks